(12) United States Patent
Hanlon

(10) Patent No.: US 11,478,446 B2
(45) Date of Patent: Oct. 25, 2022

(54) PAIN RELIEVING FORMULATIONS CONTAINING CANNABIS AND METHODS OF MAKING SAME

(71) Applicant: Teresa Ann Hanlon, River Drive Park (CA)

(72) Inventor: Teresa Ann Hanlon, River Drive Park (CA)

(73) Assignee: Teresa Ann Hanlon, River Drive Park (CA)

( * ) Notice: Subject to any disclaimer, the term of this patent is extended or adjusted under 35 U.S.C. 154(b) by 228 days.

(21) Appl. No.: 17/005,727

(22) Filed: Aug. 28, 2020

(65) Prior Publication Data

US 2022/0062221 A1   Mar. 3, 2022

(51) Int. Cl.
| | | |
|---|---|---|
| A61K 31/352 | (2006.01) | |
| A61K 31/05 | (2006.01) | |
| A61K 47/44 | (2017.01) | |
| A61K 9/00 | (2006.01) | |
| A61K 47/36 | (2006.01) | |
| A61K 31/355 | (2006.01) | |
| A61K 47/12 | (2006.01) | |
| A61K 47/10 | (2017.01) | |
| A61K 9/06 | (2006.01) | |
| A61P 29/00 | (2006.01) | |

(52) U.S. Cl.
CPC .......... *A61K 31/352* (2013.01); *A61K 9/0014* (2013.01); *A61K 9/06* (2013.01); *A61K 31/05* (2013.01); *A61K 31/355* (2013.01); *A61K 47/10* (2013.01); *A61K 47/12* (2013.01); *A61K 47/36* (2013.01); *A61K 47/44* (2013.01); *A61P 29/00* (2018.01)

(58) Field of Classification Search
CPC ...... A61K 31/352; A61K 9/0014; A61K 9/06; A61K 31/05; A61K 31/355; A61K 47/10; A61K 47/12; A61K 47/36; A61K 47/44; A61P 29/00
USPC ........................................................ 514/454
See application file for complete search history.

(56) References Cited

U.S. PATENT DOCUMENTS

| | | |
|---|---|---|
| 9,186,386 B2 | 11/2015 | Speier |
| 10,383,816 B2 | 8/2019 | Aung-Din |
| 2010/0016418 A1 | 1/2010 | Guy et al. |
| 2012/0264818 A1 | 10/2012 | Newland |
| 2020/0197359 A1 | 6/2020 | Freeze et al. |
| 2021/0052545 A1* | 2/2021 | Jones, Jr. ............... A61K 8/498 |

FOREIGN PATENT DOCUMENTS

| | | |
|---|---|---|
| CA | 3000398 A1 | 4/2017 |
| WO | 2019056123 A1 | 3/2019 |
| WO | 2019089583 A1 | 5/2019 |
| WO | 2020006599 A1 | 1/2020 |
| WO | 2020012480 A1 | 1/2020 |

\* cited by examiner

*Primary Examiner* — Kristin A Vajda
(74) *Attorney, Agent, or Firm* — Stratford Group Ltd.

(57) ABSTRACT

The present invention relates to a topically administered cannabinoid formulation that is particularly well suitable for relieving or reducing muscle, joint, and nerve pain. The formulation can be easily and painlessly applied to painful areas, and is rapidly absorbed. The formulation also comprises one or more essential oils having analgesic properties and menthol. The topical emulsified creams and lotions may comprise a full spectrum of cannabis compounds, including THC and CBD.

20 Claims, No Drawings

PAIN RELIEVING FORMULATIONS CONTAINING CANNABIS AND METHODS OF MAKING SAME

FIELD OF THE INVENTION

The present disclosure relates to pain relieving formulations, particularly to formulations containing cannabis that ease muscular, joint and neuropathic pain, more particularly to creams and lotions containing TCH and CBD.

BACKGROUND

Cannabis has long been used for medicinal purposes and as a recreational drug. The active components of cannabis, i.e. cannabinoids, are effective against nausea and vomiting, and have also been used to relieve (chronic neurogenic/neuropathic) pain that is caused by several disorders and surgical operations. Other medical indications include depression, migraine, multiple sclerosis, fibromyalgia, syndromes like Parkinson and Gilles de la Tourette and it is also used as an analgesic, spasmolytic, appetite stimulation, and a palliative and anti-convulsant medication.

Raw cannabis has a variety of health benefits, in particular cannabinoid acids found in plant material are potent anti-inflammatory agents. Decarboxylation of the naturally occurring cannabinoid acids, typically by heating, increases their bioavailability. In some instances, the decarboxylation process converts a non-psychoactive cannabinoid acid into a psychoactive cannabinoid. For example, decarboxylation of the non-psychoactive tetrahydrocannabinolic acid (THCA) produces delta-9-tetrahydrocannabinol (THC) which is psychoactive. Another common cannabinoid acid found in the cannabis plant is cannabidiolic acid (CBDA). The raw form has health-promoting properties, but the step of decarboxylation (to form cannabidiol CBD) makes it more readily available for the body to use, but it remains non-psychoactive.

THC has been found to have several therapeutic applications such as treatment of mild to moderate pain, appetite loss, insomnia, depression and nausea. Additionally, TCH can be use in the treatment of a variety of autoimmune disorders, including multiple sclerosis, colitis, lupus, and arthritis.

CBD has also been found to have several therapeutic benefits including providing relief from chronic pain due to muscle spasticity, muscle convulsions and inflammation. This type of pain is often experienced by patients who suffer from multiple sclerosis, fibromyalgia and epilepsy. In addition to pain relief CBD has been shown to alleviate general feelings of anxiety as well as cannabis-induced anxiety.

From a general therapeutic perspective THC and CBD have important effects on one another when ingested together, the so-called entourage effect. When administered together, CBD not only prolongs the effects of THC-therapy by inhibiting the breakdown process of THC by the liver, but it also appears to be able to reduce side effects of THC (Russo & Guy, 2006). Four basic mechanisms of synergy have been proposed (Wagner & Ulrich-Merzenich, 2009); (i) multi-target effects; (ii) pharmacokinetic effects such as improved solubility or bioavailability; (iii) agent interactions affecting bacterial resistance; and (iv) modulation of adverse events.

In humans, the routes of delivery of cannabis are varied. Cannabis is often mixed with tobacco and smoked. The heat generated during smoking causes the decarboxylation of the acid cannabinoids and this route of delivery has a rapid onset. For patients preferring not to smoke, or needing more localized effects, topical formulations are more suitable.

WO2020012480 discloses compositions for topical use comprising active agents to provide pain relief. The compositions comprise a magnesium salt, a cannabinoid and at least one additional topical analgesic agent. The magnesium salt is preferably magnesium sulfate or magnesium chloride. Compositions may comprise one or multiple cannabinoids, such as a combination of CBD and THC. The at least one additional topical analgesic agent may include wintergreen, eucalyptus and peppermint oil. Menthol may be present in an amount between about 0.1% and about 15% of the composition.

CA3000398 discloses natural topical and analgesic pain relief and anti-inflammation compositions and methods to reduce pain and inflammation using cannabinoid compounds, including 9-tetrahydrocannabinol (delta-9-THC), 9-THC propyl analogue (THC-V), cannabidiol (CBD). The compositions comprise a hydrophobic topical analgesic in which the carrier is a fixed plant oil or seed oil or a mixture of fixed plant and/or seed oils to form a therapeutic massage oil which may including peppermint or wintergreen oil and menthol.

WO2020006599 discloses pharmaceutical compositions comprising Δ9-tetrahydrocannabinol (THC), cannabidiol (CBD) and a terpene fraction obtained by extraction of a Cannabis plant, and their use in the treatment of pain. Treatment of patients suffering from non-cancer chronic pain with the pharmaceutical composition comprising THC and CBD and a synergistic terpene fraction may provide sufficient analgesia or antinociception to assist in pain management strategies. The pharmaceutical compositions formulated for oral administration may contain a flavouring agent such as peppermint, oil of wintergreen, or cherry flavouring.

WO2019089583 discloses formulations comprising cannabinoids. Some of the orally administered formulations contain peppermint oil, menthol and other flavorings including eucalyptus and oil of wintergreen.

U.S. Pat. No. 0,383,816 discloses A method of treating a disease state or condition in humans via topical brainstem afferent stimulation therapy via the administration of a cannabinoid drug. The invention provides a method for the treatment of weakness weakness and pain. The topical formulation releases one or more cannabinoid drugs at a predetermined rate over a defined period of time to a defined site of application.

US20200197359 discloses a topical composition comprising a terpene blend and a cannabinoid such as THC and CBD and is useful for managing pain. The formulations and compositions for a topical pain cream to be used as needed for treatment of inflammatory skin disorders and conditions and can be used directly on or under the skin. The composition is used for itching, swelling or painful joints. The composition has sufficient transdermal capability to reduce local pain of the skin, musculature, connective tissue, joints and neuropathic pain.

WO2019056123 discloses Pharmaceutical compositions comprising one or more cannabinoids and a pharmaceutically acceptable carrier are disclosed. The compositions are in a form suitable for topical administration, and are useful in the treatment of pain.

U.S. Pat. No. 9,186,386 discloses methods of obtaining an extract of cannabis plant material and processing of the extract to provide a concentrate of cannabis. The invention also provides for pharmaceutical dosage forms and methods of medical treatment that include administering the pharmaceutical dosage forms, some of which are particularly suited to topical administration. The oral formulations may contain menthol, eucalyptus and peppermint.

US20120264818 discloses topical compositions including heat-treating mature, dried, powdered cannabis sativa flower and bud leaves in carriers and methods for the treatment of pain and methicillin-resistant *Staphylococcus aureus*. The topical composition, which may include menthol, is used to treat pain, inflammation, muscle tightness, muscle spasms, skin ulcerations, and scleroderma. In one embodiment, the topical composition is used to treat joint pain, muscle pain, or arthritis.

US20100016418 discloses the use of cannabidiol (CBD) type compounds or derivative thereof and tetrahydro-cannabinol (THC) type compounds or derivative thereof in the manufacture of a medicament for the treatment of neuropathic pain. The disclosed medicaments are formulated for internal, not topical, administration.

All documents cited are incorporated herein by reference.

None of the above cited documents, alone or in combination satisfy the need for a topically administered cannabis formulation that is particularly well suited for relieving or reducing muscle, join, and nerve pain. There therefore remains a need for a formulation that can be easily and painlessly applied to painful areas, that is rapidly absorbed and can decrease joint and muscle inflammation.

BRIEF SUMMARY

It is an object of the invention to provide pain relieving formulations containing cannabis and methods of making same.

In accordance with an aspect of the invention there is provided a topical formulation comprising: an emulsifying base; a combination of two or more cannabinoids suspended in an oil; one or more essential oils; menthol; a thickening agent and a preservative.

In accordance with another aspect of the invention there is provided a method of preparing a topical formulation comprising the steps: preparing a emulsifying wax base consisting of components selected from the group consisting of: emulsifying wax; cetyl alcohol; stearic acid; virgin coconut oil; shea butter; jojoba oil; vegetable glycerin; xanthan gum; and vitamin E (D-alpha-tocopherol); heating the wax base to 70 to 75 degrees Celsius, with continuous stirring; adding a combination of two or more cannabinoids suspended in an oil to form a first phase; adding a thickening agent selected from the group consisting of: colloidal oatmeal; cetyl alcohol; stearyl alcohol; carnauba wax; stearic acid; locust bean gum; xanthan gum; gelatin; carbomers; and sodium carboxy methyl cellulose; heating distilled water and menthol crystals to 70 to 80 degrees Celsius to form a second phase; adding the first phase to the second phase and emulsifying using a high shearing mixer to produce a third phase; adding one or more essential oils to the third phase.

In accordance with yet another aspect of the invention there is provided a method for treating pain in a mammal, comprising topically administering to the mammal a combination of cannabinoids, essential oils, and menthol in a topically acceptable lotion base or cream base.

The advantages and features of the present invention will become better understood with reference to the following more detailed description and claims taken in conjunction with the accompanying drawings in which like elements are identified with like symbols.

To easily identify the discussion of any particular element or act, the most significant digit or digits in a reference number refer to the figure number in which that element is first introduced.

DETAILED DESCRIPTION

Formulations and methods for carrying out the invention are presented in terms of embodiments. However, the invention is not limited to the described embodiments, and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and the configurations shall be shown and described for purposes of clarity and disclosure and not by way of limitation of scope.

It is contemplated that formulations of the embodiments of the invention contain one of more cannabinoids, a one of more essential oils and menthol in a primary oil/emulsifying wax base. The formulations may comprise additional active and non-active compounds and a preservative.

The cannabinoids are selected from the group consisting of: THC (tetrahydrocannabinol); THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin); CBCV (cannabichromevarin); CBGV (cannabigerovarin); CBGM (cannabigerol monomethyl ether); CBE (cannabielsoin); and CBT (cannabicitran).

The cannabinoids are typically dissolved in a lipid to suspend and dilute the cannabis extracts. The lipids can be edible oils or food grade carrier oils selected from the group comprising: ajwain oil, almond oil, angelica root oil, anise oil, asafoetida oil, Balsam of Peru, camphor oil, calamodin oil, calamansi essential oil, caraway seed oil, caramom seed oil, calamus oil, chamomile oil, cinnamon oil, citron oil, citronella oil, clary sage oil, coconut oil, clove oil, coffee oil, coriander oil, costmary oil, costus root oil, cubeb oil, cypress oil, cypriol oil, curry leaf oil, davana oil, dill oil, eucalyptus oil, fennel seed oil, fenugreek oil, galangal oil, ginger oil, goldenrod oil, grapefruit oil, helichrysum oil, hickory nut oil, horseradish oil, hyssop oil, Idaho-grown tansy oil, juniper berry oil, laurus nobilis, lavender oil, ledum oil, lemon oil, lemongrass oil, lime oil, linalool oil, mandarin oil, marjoram oil, MCT oil, melissa oil, mentha arvensis oil, mint oil, moringa oil, mountain savory oil, mustard oil, myrrh oil, myrtle oil, neroli oil, nutmeg oil, oregano oil, orris oil, Palo Santo oil, parsley oil, peppermint oil, petitgrain oil, Piper nigrum L. oil, ravensara oil, Roman chamomile oil, rosehip oil, rosemary oil, rosewood oil, sage oil, star anise oil, schisandra oil, spearmint oil, soy oil, spikenard oil, star anise oil, sweet almond oil, tangerine oil, tarragon oil, thyme oil, turmeric oil, vegetable oil, wintergreen oil, yarrow oil, ylang-ylang oil, and zedoary oil.

The present invention particularly relates to topical emulsified formulations containing, but not limited to, THC and CBD. The formulations may take the form of creams or lotions which are particularly well suitable for relieving or reducing muscle, join, and nerve pain. In some embodiments of the invention, equal amounts of full spectrum THC and CBD oil are incorporated into the formulations. Both THC and CBD are used to create a therapeutic synergistic effect by binding with CB1 and CB2 receptors present on the skin.

As all embodiments of the formulations are topical, they only affect the location in which the formulation is applied. As both THC and CBD are lipophilic compounds, when they are absorbed through the skin via topical application, the THC and CBD molecules essentially enter and remain in the adipose cells. As the THC remains in the adipose cell this prevents absorption into the bloodstream and remains at the site where the formulation was applied thereby preventing the user from experience a "THC high" feeling but and improving life quality.

The essential oils may be selected from the group consisting of; arnica; birch; black pepper; cayenne; chamomile; clary; clove; copaiba; cypress; eucalyptus; frankincense; ginger; helichrysum; juniper; lavender; lemongrass; marjoram; peppermint; rosemary; sandalwood; thyme; vetiver; yarrow; and wintergreen. Many of these oils are have analgesic properties.

Specific formulations contain additional components selected from, but not limited to, almond oil, colloidal oatmeal and arnica in addition to cream or lotion base ingredients.

It is contemplated that the formulations of the invention possess various properties due to the presence and synergistic combination of different reagents. For example, the combination of essential oils and menthol crystals creates an aromatic aroma that is known to create a sense of calm and relaxation often referred to as aroma therapy benefits. Moreover, the combination of essential oils works to increase circulation where the cream is applied to aid in decreasing inflammation by bringing greater blood flow to site, increased circulation also helps to reduce excess fluid from interstitial space.

Some of the formulations of the invention contain menthol crystals which provide a local anesthetic effect with a cool numbing sensation that penetrates the skin. The presence of CBD and THC in the formulations reduce inflammation and pain by creating analgesic effect when topically applied. It has been found that the combined ingredients create and immediate effect for pain relief as well as CBD/TCH create a longer lasting pain relief benefit.

The formulations of the embodiments of the invention contain various active components. For example, wintergreen is an essential oil that contains methyl salicylate (closely related to aspirin) which creates a topical analgesic effect, it is known for producing a natural numbing effect, and it promotes circulation. Eucalyptus essential oil is known to be an antispasmodic, which eases muscle pain, and swelling, and the aroma has calming effect. Peppermint essential oil contains menthol, has cooling effect, it is also antispasmodic and anti-inflammatory effect, which promotes improved circulation, and its aroma has calming effect. Menthol crystals are a counter irritant that have a cooling effect on the skin, which distracts the brain from pain. Full spectrum CBD and THC bind to CB1 and CB2 receptors on skin and reduce inflammation and decrease sensation of pain.

Formulations of the invention function to: relieve aches and pain of muscle and joint associated with backache and neck, arthritis, strained muscles; relieve pain from peripheral nerve pain; help to decrease joint/muscle inflammation; and soothe muscle spasms.

Creating a lotion or cream takes three phases: preparing a water phase, an oil phase and a finishing or emulsifying phase. An emulsifier is necessary to form a homogenous mixture keeping the water phase and the oil phase together. Various emulsifiers are known and serve to stabilize an emulsion by increasing its kinetic stability. One class of emulsifiers is known as "surface active agents", or surfactants, which are molecules that have both lipophilic and lipophobic moieties.

In a water-in-oil emulsion, the oil surrounds the water and the oil touches the skin first. The level of greasiness depends on the formula—all of which will be absorbed into the skin. The emulsion may be made from beeswax, sodium tetraborate and water and have little to no greasiness. In an oil-in-water emulsion, the oil is surrounded by water. This method creates creams and lotions that feel moist, less greasy. When absorbed into the skin there is very little to no oily residue.

Emulsifiers come in a variety of forms. Topical formulations typically comprise an emulsifying wax, lecithin, or stearic acid. Beeswax, sodium tetraborate, cetyl alcohol and polysorbate 20 can also be used as can many other emulsifiers known in the field.

The following describes a method to prepare an exemplary formulation of an embodiment of the invention Phase One: two-step process to create the primary oil/emulsifying wax base Step one Combine the following ingredients, and heat until all ingredients are melted, stirring continually until heat reaches 70 to 75 degrees Celsius. Maintain temperature.

20% emulsifying wax
12% cetyl alcohol
12% stearic acid
20% virgin coconut oil
5% shea butter
14% jojoba oil
13% vegetable glycerin
2% xanthan gum
2% vitamin E (D-alpha-tocopherol)

Step two

Add additional specialty ingredients to primary oil/emulsifying wax base prior to adding water.

One or more thickening agent, for example; 1 gram of colloidal oatmeal per 300 gram batch of lotion.

1% sweet almond oil (weight of the CBD/THC oil is to be removed from total weight of sweet almond oil for total of 1%. The mgs of CBD and THC in the formulation are typically the same and the mg are to be equal in amounts and equal to the gram weight of total lotion. i.e. a lotion base of 600 grams should have in the region of 600 mg THC and 600 mg CBD. 1 mg of CBD/THC per 1 gram of lotion. Hence equal amounts of full spectrum CBD/THC are added to the sweet almond oil.

Phase Two

81% distilled water

Heat distilled or de-ionized (demineralized) water until temp reaches 75 degrees and maintain temperature.

Add 4% menthol crystals add to water base and full dissolve.

Combine distilled water and primary oil/emulsifying wax base from phase one together, ensure combination temperature is maintained between 70-80 degrees Celsius for proper emulsification, use a high shearing mixer to homogenize the distilled water and primary oil/emulsifying wax base until smooth.

Add 1% essential oil blend divided equally between wintergreen essential oil, peppermint essential oil, eucalyptus essential oil. Add essential oil blend when lotion cools to 60 degrees Celsius.

Use a high shearing mixer to ensure essential oil blend is fully incorporated.

Phase Three

Add 1% preservative, allow the lotion to cool down to the appropriate temperature before adding the preservative. The appropriate temperature is indicated by the manufacturer of each preservative. For example, for Optiphen, the lotion should be cooled to 80 degrees Celsius or cooler before adding the preservative.

Use high shearing mixer to fully incorporate preservative

Measure pH level and adjust if required to maintain pH balance between 5-5.5. The pH can be increased using sodium bicarbonate, and pH can be decreased by adding citric acid.

Continue to homogenize lotion base with low shear mixing until lotion base has cooled to a temperature of 35 degrees before pouring into jars/containers.

Allow lotion to full cool to room temperature before adding caps/lids to containers.

The following table is an example of the gram amounts used in the preparation of an exemplary formulation.

TABLE 1

Example recipe of 600-gram lotion batch of a lotion in accordance with an embodiment of the invention

| percentage | ingredient | 600 gram batch |
| --- | --- | --- |
| 12% | Primary lotion base | 72 grams |
| 81% | Distilled water | 486 grams |
| 1% | Essential oil blend-divided equal amounts of the 3 essential oil | 6 grams (2 grams each) |
| 4% | Menthol crystals | 24 grams |
| 1% | Sweet almond oil combined with CBD/TCH oil for total 1% | 6 grams (i.e 4 grams sweet almond oil and 2 grams CBD & THC) |
| 1% | Preservative (Optiphen) | 6 grams |
| 1 gram | Colloidal oatmeal to every 300-gram batch | 2 grams |

Additional embodiments of the invention feature the following variations to this recipe.

One variation to this recipe would be infusing the jojoba with plant extracts such as arnica. Arnica is an herb that has been used for centuries as an anti-inflammatory and analgesic, decreases bruising by reducing healing time from bruising. So this would be beneficial for more acute type injuries such as bruising and pulled muscle. For example, jojoba could be infused at a value of 113 g herb per 1000 ml of oil, to give a concentration of 11.3% dry herb/L of oil.

Yet another variation would be to increase the amount of CBD/THC used i.e. 2 to 1 ratio/2 mg of CBD/THC to 1 gram of lotion. Hence the this would be equivalent to 2 mg of THC +2 mg of CBD per gram of lotion.

Common types of topical formulations comprise; creams, lotions, salves, ointments, gels and pastes. There are several factors to consider when choosing a topical preparation. For example, an occlusive vehicle enhances penetration of the active ingredient and improves efficacy. Also, the vehicle itself may have a cooling, drying, emollient, or protective action. It can also cause side effects by being excessively drying or occlusive. The formulation should match the site of application, greasy formulations should be avoided for weepy lesions, and gels or lotions are more suitable for hairy areas. It is also important to consider irritation or sensitization potential. Generally, ointments and water in oil creams are less irritating, while gels may be more irritating. Ointments do not contain preservatives or emulsifiers if allergy to these agents is a concern.

Creams are an emulsion of water and oil, classified as oil in water or water in oil emulsions. Oil in water creams tend to spread easily and do not leave the skin greasy and sticky, whereas water in oil creams are more greasy and more emollient.

Lotions includes any liquid preparation in which inert or active medications are suspended or dissolved. An oil in water emulsion, with a high water content to give the preparation a liquid consistency can be considered a lotion. Most lotions are aqueous or hydroalcoholic systems, wherein some preparations may contain a small amount of alcohol to aid solubilization of the active ingredients and to increase the rate of evaporation of the solvent from the skin surface, but are not suitable for application to broken skin. Lotions are easy to apply to large areas and are suitable for hairy areas, or to be dabbed onto sensitive or painful areas.

Ointments are semi-solid preparations of hydrocarbons (petrolatum, mineral oil, paraffins, synthetic hydrocarbons) that produce an occlusive effect which enhances penetration of active substances into the skin, thereby improving efficacy of delivery.

According to the various embodiments of the invention, the composition may be in the form of a cream, lotion, ointment, paste, gel, suspension, pump spray, aerosol spray, non-pressurized spray, continuous spray, non-chlorofluorocarbon-based spray, aerosol foam, liquid, solution, powder, stick, roll-on or patch.

In addition to active ingredients, compositions described herein may further comprise at least one inert ingredient. The inert ingredient may be selected from the group consisting of: water, a solvent, an emulsifier, an emollient, a moisturizer, a pH adjustment agent, a polymer, a humectant, an occlusive agent, a preservative, a thickener, an anti-irritation agent, a conditioning agent, a buffer, a vitamin, an extract, a natural oil, a wax, a penetration enhancer, a peptide, a sugar derivative, a fatty acid, a fatty alcohol, a silicone, a polyethyl-glycol, a fragrance, a pigment, an ester, a triglyceride, a butter, hyaluronic acid, and an absorbing powder.

These novel topically administered compositions and methods relieve inflammation and pain associated with one or more of nociceptive, neuropathic, somatic pain, radicular pain and associated musculoskeletal, osteoarthritic, muscle, joint, arthritis, rheumatoid arthritis, back, strains and sprains pain associated with sports injuries, post-surgical conditions and other diseases.

As used herein, "arthritis" refers to inflammation of the bone fascia producing pain and immobility. "Joint inflammation" refers to an inflammatory response occurring in the bone joints, producing pain and immobility. "Joint pain" refers to pain associated with the relative motion of two or more bones at a mutual joint thereof. "Neuropathic pain and spasticity" refers to pain and loss of muscle control produced by damage or disease that affects the somatosensory system, which can results from injury or disease of the central or peripheral nervous systems.

With regard to usage, for adults and children over 12 years of age. Apply to affected area up to 4 times daily. Take small amount of cream and massage over sore, tired muscles and joints. Do not exceed daily recommended use. For use with children 12 years of age and younger consult a physician prior to use.

It will be understood by a worker in the field that the formulations of the various embodiments of the invention are for external use only. They must not be used on open or damaged skin. Contact with eyes and mucus membranes must be avoided. If skin irritation or rash occur, use should be discontinued. The formulations should not be used on pregnant or lactating females. The formulations should not be applied immediately after bath, wait ½ hour. Neither should they be used with tight fitting tensor bandages or with heating pads. A physician should be consulted prior to using products containing CBD/THC and essential oils. If conditions do not improve over 7 days, or if symptoms become worse a physician should be consulted. The formulations should be kept out of reach of children and if ingested a Poison Control Centre or physician must be contacted immediately. The formulations should be stored in a cool dry place.

The foregoing descriptions of specific embodiments of the present invention have been presented for purposes of illustration and description. They are not intended to be exhaustive or to limit the invention and method of use to the precise forms disclosed. Many modifications and variations are possible in light of the above teaching. The embodiments described were chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

The invention claimed is:

1. A topical formulation comprising:
   an emulsifying base consisting of components selected from the group consisting of: emulsifying wax; cetyl alcohol; stearic acid; virgin coconut oil; shea butter; jojoba oil; vegetable glycerin; xanthan gum; vitamin E (D-alpha-tocopherol); lecithin; beeswax; sodium tetraborate; and polysorbate 20;
   a combination of two or more cannabinoids suspended in an oil;
   one or more essential oils;
   menthol;
   thickening agent; and
   a preservative.

2. The topical formulation of claim 1, wherein the two or more cannabinoids are selected from the group consisting of: THC (tetrahydrocannabinol); THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin); CBCV (cannabichromevarin); CBGV (cannabigerovarin); CBGM (cannabigerol monomethyl ether); CBE (cannabielsoin); and CBT (cannabicitran).

3. The topical formulation of claim 2, wherein the two or more cannabinoids are THC (tetrahydrocannabinol) and CBD (cannabidiol).

4. The topical formulation of claim 3, wherein the THC and CBD are in the formulation present in equal amounts.

5. The topical formulation of claim 4, wherein the THC and CBD are each present at an amount between 0.1 to 0.5 wt % of the total formulation.

6. The topical formulation of claim 1, wherein the one or more essential oils are selected from the group consisting of: arnica; birch; black pepper; cayenne; chamomile; clary; clove; copaiba; cypress; eucalyptus; frankincense; ginger; helichrysum; juniper; lavender; lemongrass; marjoram; peppermint; rosemary; sandalwood; thyme; vetiver; yarrow; and wintergreen.

7. The topical formulation of claim 6, wherein the one or more essential oils are eucalyptus, peppermint, and wintergreen.

8. The topical formulation of claim 1, wherein the menthol is present at between 2 to 6 wt %.

9. The topical formulation of claim 8, wherein the menthol is present at 4 wt %.

10. The topical formulation of claim 1, wherein the emulsifying base consists of: emulsifying wax; cetyl alcohol; stearic acid; virgin coconut oil; shea butter; jojoba oil; vegetable glycerin; xanthan gum; and vitamin E (D-alpha-tocopherol).

11. The topical formulation of claim 10, wherein the emulsifying base consists of:
    20% emulsifying wax;
    12% cetyl alcohol;
    12% stearic acid;
    20% virgin coconut oil;
    5% shea butter;
    14% jojoba oil;
    13% vegetable glycerin;
    2% xanthan gum; and
    2% vitamin E (D-alpha-tocopherol).

12. The topical formulation of claim 1, wherein the thickening agent is selected from the group consisting of: colloidal oatmeal; cetyl alcohol; stearyl alcohol; carnauba wax; stearic acid; locust bean gum; xanthan gum; gelatin; carbomers; and sodium carboxy methyl cellulose.

13. The topical formulation of claim 12, wherein the colloidal oatmeal is present at between 3 to 4 wt %.

14. The topical formulation of claim 1, wherein the two or more cannabinoids are suspended in sweet almond oil.

15. The topical formulation of claim 1, wherein the preservative is phenoxyethanol and an emollient base.

16. The topical formulation of claim 10, wherein the jojoba is infused with arnica.

17. A method of preparing a topical formulation comprising the steps:
    preparing a emulsifying wax base consisting of: emulsifying wax; cetyl alcohol; stearic acid; virgin coconut oil; shea butter; jojoba oil; vegetable glycerin; xanthan gum; and vitamin E (D-alpha-tocopherol);
    heating the wax base to 70 to 75 degrees Celsius, with continuous stirring;
    adding a combination of two or more cannabinoids suspended in an oil to form a first phase;
    adding a thickening agent selected from the group consisting of: colloidal oatmeal; cetyl alcohol; stearyl alcohol; carnauba wax; stearic acid; locust bean gum; xanthan gum; gelatin; carbomers; and sodium carboxy methyl cellulose;
    heating distilled water and menthol crystals to 70 to 80 degrees Celsius to form a second phase;
    adding the first phase to the second phase and emulsifying using a high shearing mixer to produce a third phase;
    adding one or more essential oils to the third phase.

18. The method of claim 17, wherein the two or more cannabinoids are THC and CBD and the one or more essential oils are selected from the group consisting of: wintergreen essential oil; peppermint essential oil; and eucalyptus essential oil.

19. A method for treating pain in a mammal, comprising topically administering to the mammal the topical formulation of claim 1.

20. The method for treating pain of claim 19, wherein the pain is associated with one or more of nociceptive, neuropathic, somatic pain, radicular pain and associated musculoskeletal, osteoarthritic, muscle, joint, arthritis, rheumatoid arthritis, back, strains and sprains pain associated with sports injuries, post-surgical conditions, inflammation and other diseases.

* * * * *

UNITED STATES PATENT AND TRADEMARK OFFICE
CERTIFICATE OF CORRECTION

| | | |
|---|---|---|
| PATENT NO. | : 11,478,446 B2 | |
| APPLICATION NO. | : 17/005727 | |
| DATED | : October 25, 2022 | |
| INVENTOR(S) | : Teresa Ann Hanlon | |

It is certified that error appears in the above-identified patent and that said Letters Patent is hereby corrected as shown below:

In the Specification

Column 2, Line 40, delete "0,383,816" and insert --10,383,816--; and
Column 2, Line 44, delete the second occurrence of "weakness".

Signed and Sealed this
Third Day of January, 2023

Katherine Kelly Vidal
*Director of the United States Patent and Trademark Office*